United States Patent [19]
Dimarogonas

[11] Patent Number: 5,652,386
[45] Date of Patent: *Jul. 29, 1997

[54] METHOD AND APPARATUS FOR PREDICTING STURCTURAL INTEGRITY BY ESTIMATING MODAL DAMPING FACTOR

[75] Inventor: Andrew D. Dimarogonas, St. Louis, Mo.

[73] Assignee: Washington University, St. Louis, Mo.

[*] Notice: The term of this patent shall not extend beyond the expiration date of Pat. No. 5,402,781.

[21] Appl. No.: 473,270

[22] Filed: Jun. 7, 1995

Related U.S. Application Data

[63] Continuation-in-part of Ser. No. 25,940, Mar. 3, 1993, Pat. No. 5,476,009.
[51] Int. Cl.⁶ ............................................. G01N 29/04
[52] U.S. Cl. ............................ 73/582; 73/810; 364/508
[58] Field of Search ........................... 73/575, 579, 582, 73/584, 587, 589, 583, 808, 810, 811, 809; 364/507, 508, 571.05, 506

[56] References Cited

U.S. PATENT DOCUMENTS

| | | | |
|---|---|---|---|
| 3,106,838 | 10/1963 | Crooks | 73/582 |
| 3,153,338 | 10/1964 | Kleesattel | 73/573 |
| 3,531,982 | 10/1970 | Clotfelter et al. | 73/582 |
| 3,744,299 | 7/1973 | Bliss | 73/595 |
| 3,857,279 | 12/1974 | Salzer et al. | 73/582 |
| 4,064,745 | 12/1977 | Gaddum | 73/805 |
| 4,542,639 | 9/1985 | Cawley et al. | 73/582 |
| 5,210,704 | 5/1993 | Husseiny | 364/506 |
| 5,305,645 | 4/1994 | Reifsnider et al. | 73/808 |

OTHER PUBLICATIONS

*Structural Damping*, a paper presented at a colloquium on structural damping held at the American Society of Mechanical Engineering annual meeting, pp. 1–34, Dec. 1959.

52 *Calcified Tissue International* 244–47, article entitled Material Damping for Monitoring of Density and Strength of Bones, by Andrew D. Dimarogonas et al., 1993.

*Primary Examiner*—Christine K. Oda
*Attorney, Agent, or Firm*—Howell & Haferkamp, L.C.

[57] ABSTRACT

The integrity of structures may be determined by either one of two methods. In a first method, an impulse of energy is introduced into the structure, such as by striking the structure, and the induced vibration is measured and the modal damping factor is calculated, the modal damping factor being directly related to the integrity of the structure. In a second method, a continuous energy input is provided to the structure for inducing a continuous vibration in the structure. This continuous vibration is measured with a transducer and a modal damping factor is calculated with a computer. The computer uses an algorithm to estimate the modal damping factor of the structure by calculating a theoretical response of an idealized system from several assumed parameters and varying those parameters until the difference between the measured response of the structure and a theoretical response of the idealized system is within an acceptable margin of error.

18 Claims, 3 Drawing Sheets

```
Algorithm FindDampingFactor:
  Open File RAW.DAT for read
        Read number of samples (n)
        Read time interval (Δt)
        Read minimum frequency f_min
        Read maximum frequency f_max
        Read n samples x(1),x(2),....,x(n)
  Close the file RAW.DAT
  Plot function x(i) vs the time (i-1)Δt
  Select the desired maximum value x_max of x(i), i=1,2,....,n at the
      desired mode at i=i_0
  Find natural frequency f_n=f_min+(i_0-1)(f_max-f_min)/n
  Find natural frequency in rad/sec ω_a=2πf_a
  Select the desired limits of frequency before and after the selected
      frequency,points of the spectrum,i_1 and i_2
  Assume value ζ of the damping factor
  ....Find an improved guess for ζ using the Newton's Method on ζ
          keeping ω_a x_max constant
  Do
    Call ErrorFunction (i_1,i_2,n,[x(i),i=1,2,....,n],x_max,ζ,ω_a,f_max,f_min,c_0)
    Call ErrorFunction (i_1,i_2,n,[x(i),i=1,2,....,n],x_max,ζ+Δζ,ω_a,f_max,f_min,c_0+Δc)
    Correction=Δζc_0/Δc
    ζ=ζ-Correction
  Loop until |Correction|<Preset value
  ...Find the solution ζω_a x_max using the Newton's Method
  Select step a
  Select step δ
  Select precision φ_max
  Do
    Do
      Call ErrorFunction(i_1,i_2,n,[x(i),i=1,2,....,n],x_max,ζ,ω_a,f_max,f_min,c_0)
      Call ErrorFunction(i_1,i_2,n,[x(i),i=1,2,....,n],x_max+a,ζ,ω_a,f_max,f_min,c_0)
      Call ErrorFunction(i_1,i_2,n,[x(i),i=1,2,....,n],x_max,ζ+a,ω_a,f_max,f_min,c_0)
      Call ErrorFunction(i_1,i_2,n,[x(i),i=1,2,....,n],x_max,ζ,ω_a+a,f_max,f_min,c_0)
      d_x=(c_x-c_0)/a;  d_t=(c_t-c_0)/a;  d_ω=(c_ω-c_0)/a
      sum=√(d_x^2+d_t^2+d_ω^2)
      x_max=:x_max-δd_x/sum
      ζ =:ζ-δd_t/sum
      ω_a=:ω_a-δd_ω/sum
      e =√(δd_x^2+δd_t^2+δd_ω^2)/sum
      c_prev=c
      Call ErrorFunction(i_1,i_2,n,[x(i),i=1,2,....,n],x_max,ζ,ω_a,f_max,f_min,c)
    Loop until c_prev<c
  Loop until φ<φ_max
  Print "RESULTS"
  Print "Damping factor / natural frequency";
  Print ζ ω_a
END of Algorithm FindDampingFactor Algorithm ErrorFunction (i_1,i_2,n,[x(i),i=1,2,....,n],x_max,ζ,ω_a,f_max,f_min,c_0)
  ...Find response of a single-degree-of-freedom system y_i at t_i=(i-1)Δt,i=1,2,....,n
  ω_i=2π(i-1)(f_max-f_min)/n
  y_i=2x_max√(1-ζ^2)/√[[(ω_i/ω_n)^2-1]^2+(2ζω_i/ω_n)^2]
    ....Find the error
       η
  e = Σ [x(i)-y_i]^2
      i=η
End of Algorithm ErrorFunction
```

FIG. 5

METHOD AND APPARATUS FOR PREDICTING STURCTURAL INTEGRITY BY ESTIMATING MODAL DAMPING FACTOR

This application is a continuation-in-part of U.S. Pat. No. 5,476,009 filed Mar. 3, 1993 and issued Dec. 19 1995, entitled, "Method and Apparatus for Determining Material Fatigue by Measuring Damping Factors".

BACKGROUND AND SUMMARY OF THE INVENTION

There are many applications wherein structures are subjected to loads which, over time, have a tendency to fatigue the material and create a risk of failure. Thus, it is highly desirable to be able to test these structures to determine the remaining fatigue life such that they might be replaced or renewed prior to failure. In still other instances, and especially for critical applications involving health and safety, standards have been established for the routine testing of certain parts prior to their being placed in service to ensure against failure of the part. In those applications, techniques have been developed and are available in the prior art to achieve such testing. These techniques include radiographic inspection, florescent penetrant inspection, destructive testing of selected parts from a lot, and other techniques, all of which are well known in the art. However, these techniques are all subject to certain drawbacks such as expense, inconvenience, and in some cases failure to entirely eliminate or predict the premature failure of the part.

Still another situation in which these kinds of tests are conducted involve many instances where materials or parts are welded and the integrity of the weld must be verified prior to the equipment being placed in service. One particular application, from amongst many, involves the federal safety standards which govern the construction of nuclear power plants. Certain welds in certain critical equipment contained within the plant are subjected to radiographic inspection and other kinds of testing in order to verify their integrity prior to the plant being placed in service. A nuclear power plant presents perhaps an extreme example of the potential harm which might befall not only the people involved but the public at large should a critical piece of equipment suffer a premature failure. There are a myriad of other applications perhaps considered not as critical but which also are important to the health and safety of many people, including the public at large.

Because the various types of testing described above are used to predict various types of failure modes involving crack initiation and propagation other than fatigue, these testing techniques will be referred to collectively as structural integrity testing. The resulting determinations made through structural integrity testing include the amount of part life used in units of time or cycles, the amount of part life remaining in time or cycles, and the size of the largest characteristic flaw. As appreciated by those in the art, these quantities aid in the analysis and management of the structures being analyzed. For instance, an aircraft fleet operator may perform a cost-benefit analysis to determine whether a particular part should be retired or returned to service.

Despite the fact that structural integrity testing has been used for some time, and the relationship of damping to fatigue has been well known for some time, the inventor is not aware of any other efforts in the prior art to utilize the relationship between damping and fatigue in the arenas of predicting failure and determining structural integrity. For example, in a paper presented at a colloquium on structural damping at the American Society of Mechanical Engineers (A.S.M.E.) Annual Meeting in December 1959, the phenomenon of plastic strain was analyzed. In particular, damping was found to be a function of stress history and stress amplitude. As concluded in the paper, at low stresses and intermediate stresses, i.e. stresses below fifty percent of the fatigue limit, damping was not seen to be affected by the stress history of the material. On the other hand, at high stresses, i.e. stresses above fifty percent of the fatigue limit, where large plastic strain damping may be observed, stress history played a part in affecting plastic strain, as measured by the modal damping factor. Stated differently, data were presented indicating that at low and intermediate stress, the modal damping factor does not change with the number of fatigue cycles. However, above a critical stress, damping increases with the number of fatigue cycles thereby indicating that stress history and stress amplitude play a part in modal damping factor under these conditions. Although this article treated the interrelationship between stress history and stress amplitude, and their effect on damping, there was no disclosure or suggestion of using a measured modal damping factor as an indicator of structural integrity. As stated therein, the article focused on how stress history and amplitude might produce a particular modal damping factor but not how a measured modal damping factor could be used as a predictor of relative fatigue in a part. See *Structural Damping*, A.S.M.E. Proceedings, (Jerome E. Ruzicka ed., 1959).

In order to solve these and other problems in the prior art, and as a departure from the teachings in the prior art, the inventor herein has succeeded in developing the technique of measuring the modal damping factor of a discrete portion of a structure, such as a part in an assembly or the like, and using that modal damping factor for determining the structural integrity of that part either by comparing it with a standardized modal damping factor or with previously measured modal damping factors for the same part. The part might be a single piece of material, or it might be a welded or otherwise joined piece of material and the test may be one for integrity as might be required for a new part, or the test might be conducted for determining the fatigue in the part after having been installed and used over time. For new part testing, it is anticipated that standardized modal damping factors may be determined and available for comparison with the measured modal damping factor for the new part. Alternately, the modal damping factor of a series of identical new parts might be measured and used to cull out those new parts which evidence signs of manufactured flaws such as cracks, voids, or other defects. After a part has been installed and used over a period of time, a modal damping factor measurement may be made periodically as an indication of the level of fatigue the part has undergone. This technique may be used to identify parts which are in need of replacement prior to any chance of failure. In addition, there are other applications and situations in which the modal damping factor measurement of a structure might be used to good advantage. Thus, these particular examples are given as exemplary and are not intended to limit the scope of the invention described herein.

In making the modal damping factor measurement, the inventor has also succeeded in developing a simple but effective and accurate technique for measuring the modal damping factor using either of two methods. In the first method, an impulse of energy is applied to the part, such as by striking the part with a blunt object or the like, and the induced vibration in the part is measured by a transducer which converts the vibration into an electrical signal for input to a computer. A computer may used to make the appropriate calculations from the induced vibration to determine the modal damping factor as is well known in the art. Generally, the modal damping factor of a part vibrating at its natural frequency from an impulse input may be determined by comparing peak displacement amplitudes of successive cycles of the vibration. In the second method, a continuous stream of energy is input to the part instead of an impulse of energy. In a preferred embodiment, a frequency generator and amplifier may be coupled to a transducer, such as a speaker, shaker, or other such device, and the frequency generator tuned or adjusted so as to sweep through the range of the lowest natural frequencies of the part. As the frequency of the input is changed, the peak displacement amplitude of the part will vary. The modal damping factor may be readily calculated by measuring the half-power bandwidth of a cycle of displacement and dividing it by the displacement amplitude at the center frequency, as will be explained in greater detail below. Using either of these methods, a vibration is induced in the part and is measured to determine the modal damping factor.

Digital computer analysis techniques typically sample data at time intervals. This discrete sampling presents inaccuracies and computational difficulties in analyzing the part response as is well known in the art and further compounds the analysis difficulties due to noise. In order to solve these problems caused by discrete sampling, the inventor has succeeded in developing a computer algorithm which estimates the modal damping factor from discrete vibration data received from the part. The algorithm matches the measured response with a theoretical one degree of freedom system response and varies the theoretical system parameters until a suitable correlation between the theoretical and actual responses is achieved. When the suitable correlation is achieved, the actual part modal damping factor is estimated to be that of the theoretical system.

One of the advantages of using the inventor's method of inducing a vibration in the part is that it is believed that the part need not be isolated and may be tested in place within an assembly or other structure. This eliminates disassembly of the part from any larger assemblage which dramatically reduces any cost involved in using the present method in determining the modal damping factor. This provides great advantages over other prior art methods which require disassembly and isolation of the part to be tested, such as during most radiographic inspection. Furthermore, the device used to implement the method disclosed herein may be relatively compact, readily portable, and sufficiently small such that the testing of many different parts which might be otherwise relatively difficult to access may be readily achieved.

While the principal advantages and features of the present invention have been described above, a more complete and thorough understanding of the invention may be attained by referring to the drawings and description of the preferred embodiment which follow.

BRIEF DESCRIPTION OF THE DRAWINGS

FIG. 5 is a logic listing of a computer program used to estimate the part modal damping factor.

DETAILED DESCRIPTION OF THE PREFERRED EMBODIMENT

Figure 1:
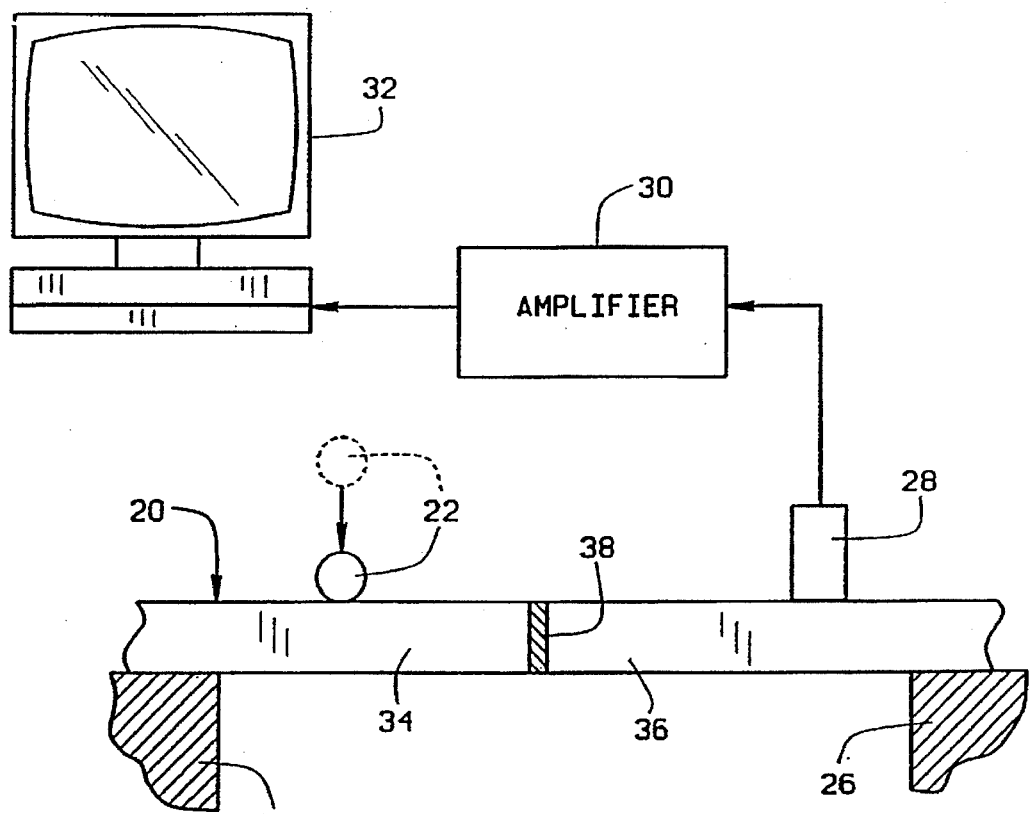
FIG. 1 is a diagrammatic view of the inventor's first technique for measuring material integrity utilizing an impulse of energy input to induce a vibration into the material.
Figure 2:
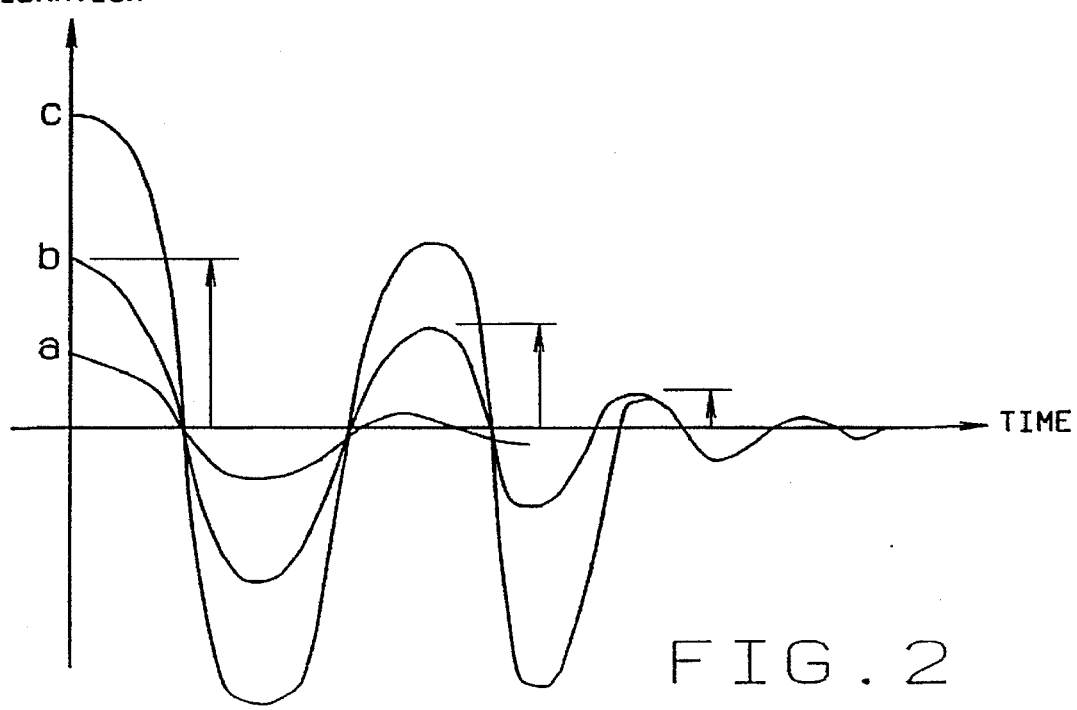
FIG. 2 is a graph of the harmonic response of vibrations induced in the material through the technique shown in FIG. 1.

As shown in FIGS. 1 and 2, the inventor's first technique for measuring structural integrity of a part includes the step of inducing a vibration in the part which is desired to be measured, such as by striking the part 20 with a blunt instrument such as a rod 22 to thereby induce vibrations in the part 20. For convenience, the opposite ends of the part 20 may be supported by a pair of supports 24, 26. A mechanoelectrical vibration transducer 28 measures the induced vibration of the part 20 and produces an electrical output which is amplified by an amplifier 30 and then input to a computer 32 for calculation of the modal damping factor.

As shown in FIG. 2, the vibration induced by the input of an impulse of energy into the part 20 will have a different initial amplitude corresponding to varying input force levels. However, the ratio of the amplitudes of the first and second cycles of vibration ($A_1/A_2$) is invariant with respect to the level of the force input to the part. Thus, the modal damping factor may be calculated by comparing the amplitudes of successive cycles of vibration induced by any of these input force levels. As shown in FIG. 2, the intensity of the blow to the part does not affect the measurement of the modal damping factor as the modal damping factor is determined by comparing two successive amplitudes and the ratio of two successive amplitudes is constant regardless of their size. Whether the initial amplitude has an intensity of a, b, or c, there is no variation in the measured modal damping factor. Instead, the modal damping factor is predominantly dependent on the characteristics of the part 20.

As shown in FIG. 1, the part 20 may be comprised of a pair of components 34, 36 which are joined by a weld 38 or the like. If that is the case, then the integrity of the weld 38 may be readily determined by the measurement of the modal damping factor. Similarly, the joint, shown in FIG. 1 as weld 38, may be any other joint or connection and its integrity similarly measured through the methodology disclosed herein.

Figure 3:
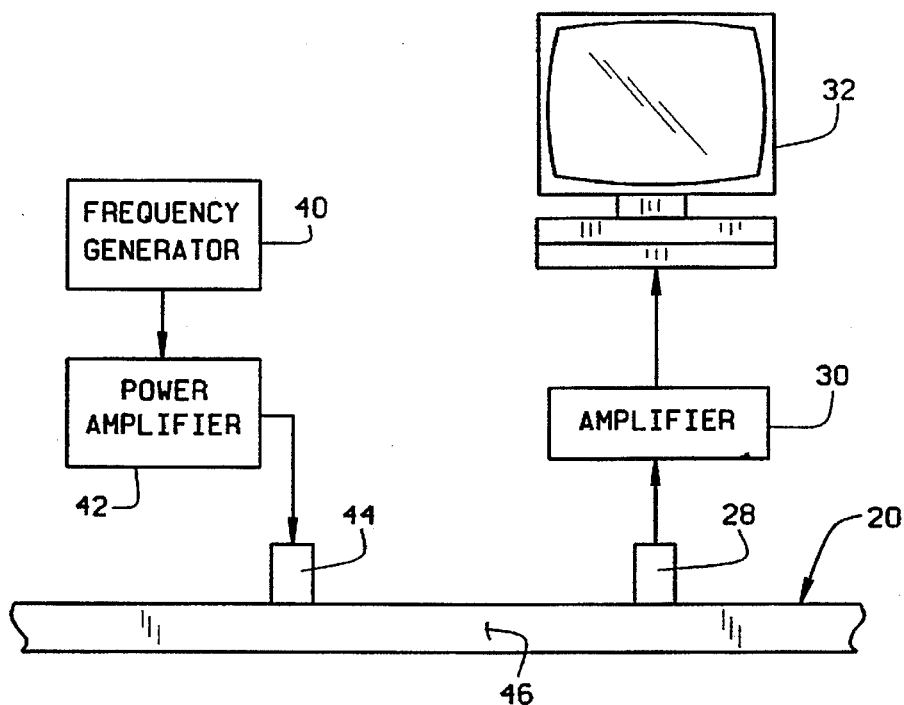
FIG. 3 is a diagrammatic view of the inventor's second technique for measuring material integrity through the coupling of a continuous energy source to the material.
Figure 4:
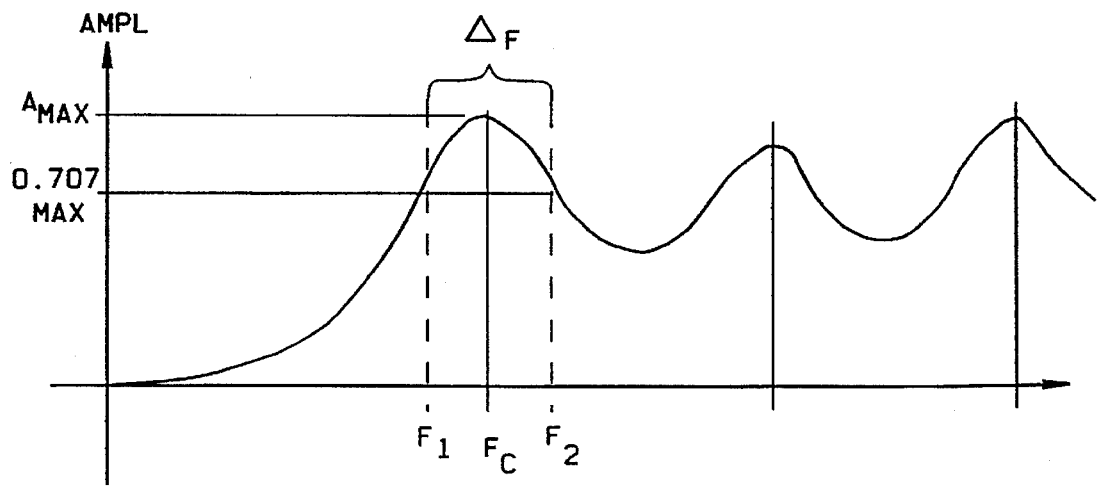
FIG. 4 is a graph of the vibrational response induced in the material using the technique of FIG. 3.

As shown in FIGS. 3 and 4, an alternate technique for measuring the modal damping factor and, hence, the part structural integrity, may be used. As before, the vibration in the part 20 is picked up by a transducer 28 and converted to an electrical signal which may then be amplified by an amplifier 30 and input to a computer 32. However, the initial energy input to the part 20 is achieved by way of a frequency generator 40 which produces an electrical output at a particular frequency which is then amplified by a power amplifier 42 which changes the amplitude of the signal output from the frequency generator. The output from the power amplifier is fed to a second transducer 44, which may be a speaker or shaker or other such electro-mechanical vibration transducer coupled to the part 20. The frequency generator 40 is then tuned to frequencies sweeping through a range of the lower natural frequencies of the part 20 to produce a continuous vibrational response therein as shown in FIG. 4. A maximum amplitude of one of the several natural frequencies induced in the part 20 is chosen for measurement of the modal damping factor. As is well known in the art, the modal damping factor $2\zeta$ is equal to the half power bandwidth, $\Delta F$, or F2–F1, divided by the center frequency, $F_c$. The center frequency, $F_c$, is the frequency at which the maximum amplitude occurs. The half power frequencies, F1 and F2, are those frequencies at which the amplitude is ($\sqrt{2}$)/2, or about 0.707 times the maximum amplitude. The existence of a crack 46 would affect the vibrational response of the part 20 and, hence, the modal damping factor measured with the inventor's technique, thereby becoming detected for suitable correction thereto.

Either or both of these techniques may be conveniently used to determine the modal damping factor of a particular part. The modal damping factor may be periodically measured for a particular part to develop a history thereof and thereby be used to monitor the developing fatigue in the part as an aid to deciding when it should be replaced or repaired. Alternately, the modal damping factor measured by the techniques disclosed and claimed herein could be used by comparing them with standardized modal damping factors for similar kinds of metals and parts.

In the preferred embodiment, and as shown in the drawings, stand alone personal computers (PC's) are depicted. However, as is well known to those of ordinary skill in the art, portable PC's are well known and readily available commercially such that a suitable device for portable use and application could readily be achieved. Furthermore, although the inventor has not developed any such device, a custom made "modal damping factor calculator" which only uses those computer elements required including, e.g., a computer chip, a custom readout, and keyboard or other data entry means, could readily be designed. Additionally, hard copy readout could readily be provided. It is intended that all of these alternatives be included within the scope of the present invention.

The microprocessor of the preferred embodiment uses the algorithm shown in FIG. 6 to analyze the response to the continuous excitation. The microprocessor may be based on a PENTIUM processor chip or the like as is well known in the art. PENTIUM is a U.S. registered trademark of the Intel Corporation.

The frequency of the input is varied over time and the response is sampled over a range of input frequencies. These responses are stored as values representing the amplitude of displacement taken at spaced time intervals corresponding with the sampling rate. These stored amplitude values lay on a curve like that shown in FIG. 4 and may be processed as described above with respect to the second method of determining modal damping factor. Because of minor noise in the response signal as well as the discrete rather than continuous sampling used, the center frequency and half power frequencies of the stored data are difficult to determine with the precision desired. Thus, the data is matched to an idealized theoretical response and the modal damping factor of the response is estimated as the modal damping factor of the theoretical system.

The system dynamics calculations are simplified by idealizing the behavior of the part as a one degree of freedom system with simple second order response as is well understood in the art. For such an idealized system, the amplitude of the response, $Y_i$, varies with the input frequency, $\omega_i$, as follows:

$$y_i = \frac{2x_{max}\zeta\sqrt{1-\zeta^2}}{\sqrt{\left[\left(\frac{\omega_i}{\omega_n}\right)^2 - 1\right]^2 + \left(2\zeta\frac{\omega_i}{\omega_n}\right)^2}}$$

were $x_{max}$ equals the maximum theoretical amplitude which occurs at the center frequency, $F_c$, of the particular mode being analyzed. As described earlier, $\zeta$ is the modal damping factor of the part for the mode being analyzed, and $\omega_n$ is the natural frequency in radians per second of the part at the maximum theoretical amplitude, $x_{max}$. It is readily apparent that $\omega_n$ and $F_c$ are different expressions for the same quantity; however, one is expressed in cycles per second ($F_c$) and the other is expressed in radians per second ($\omega_n$).

The computer algorithm shown in FIG. 5 minimizes the difference between the measured amplitudes and the theoretical amplitudes by varying the maximum amplitude ($x_{max}$), the modal damping factor ($\zeta$), and the natural frequency ($\omega_n$). As is common in the art, the difference or error between the samples and the theoretical amplitudes is evaluated by summing the squares of the differences of the values over the entire range of samples. This evaluation method is known as a least squares error evaluation. Although many different iterative numerical analysis techniques could be used, the inventor uses the Newton-Raphson iteration method to minimize the error. The Newton-Raphson method, also known as Newton's method, is an iterative process whereby an initial value or guess for a solution is assumed and a next value or improved guess is calculated by adjusting the previous guess by an increment equal to the quantity of the function at the last guess divided by the slope of the function at the last guess. In other words, $$x_{n+1} = x_n - \frac{f(x_n)}{f'(x_n)}$$

This iteration method is used because of its simplicity and relative speed of convergence to a solution. As with any iterative analytical approach, the process of improving the guess is repeated until the guess converges to a solution having an error less than some specified value. Because of the nomenclature used in many common computer languages, each iterative process is commonly referred to as a "do-loop".

In the first do-loop of the algorithm shown in FIG. 5, the Newton-Raphson method is used to obtain a good initial guess for the modal damping factor. The natural frequency and maximum amplitude are held constant while the modal damping factor is varied until the amount of change in modal damping factor is within a specified value (i.e., "|correction|<preset value"). Once this improved initial guess is found, the algorithm continues to a second do-loop.

In the second do-loop, the Newton-Raphson method is again used; however, this time the modal damping factor, natural frequency and maximum amplitude are each varied and a separate value for the error and the change in error with respect to the change in each of the three parameters is calculated. The parameters are varied until the sum of the squares of the differences of the errors is minimized. When the sum is minimized, the theoretical amplitudes are close to the sample amplitudes over the entire range of samples. Thus, the theoretical modal damping factor and the theoretical natural frequency when the sum of the squares of the differences in the errors is minimized are a good estimate of the actual modal damping factor and natural frequency of the part being analyzed. Therefore, a modal damping factor may be accurately estimated for the system even though the system response has small noise fluctuations and is only discretely sampled.

It should readily be appreciated that other iterative analysis and/or curve fitting techniques may also be used to minimize the difference between the measured and theoretical amplitudes and modal damping factors. Further, the Newton-Raphson method may be used in different ways to arrive at a solution. For instance, the first do-loop for finding an improved initial guess for modal damping factor could be eliminated if desired or supplanted by other do-loops in which improved initial guesses for natural frequency or maximum amplitude are found. Likewise, other error evaluation techniques can be used to measure the error between the theoretical and measured amplitudes. Yet another variation of the analysis technique is to use a simplified higher degree of freedom system or higher order system approximation for the theoretical amplitude calculation. Each of these variations in analysis technique are within the scope of this invention.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A device for determining a modal damping factor of a structure, the device comprising:

a transducer for measuring a vibrational response of the structure;

a computer connected to the transducer, the computer having means for matching a theoretical response of an idealized system to the measured response of the structure and means for calculating a modal damping factor of the idealized system having the matched theoretical response, the idealized system modal damping factor being representative of the modal damping factor of the structure.

2. The device of claim 1 wherein the matching means includes means for fitting a curve to a plurality of measured response data points.

3. The device of claim 2 wherein the fitting means includes means for repetitively estimating said curve to thereby minimize any difference between the curve and said plurality of measured data points.

4. The device of claim 3 wherein the fitting means includes means for adjusting any one or more of a modal damping factor, a damped natural frequency, and a maximum amplitude between estimations.

5. The device of claim 4 wherein the adjusting means includes a Newton-Raphson computational analysis technique for determining how much adjustment is made.

6. The device of claim 5 wherein the fitting means includes means for determining a difference between each measured data point and the curve with a least squares error evaluation.

7. The device of claim 6 wherein said device further comprises means for determining an integrity of said structure by comparing said calculated modal damping factor with a base modal damping factor.

8. The device of claim 7 wherein said integrity determining means includes means for comparing said calculated modal damping factor with a standardized modal damping factor.

9. The device of claim 7 wherein said integrity determining means includes means for comparing said calculated modal damping factor with an historical modal damping factor for said structure.

10. A method for determining a modal damping factor of a structure, the method comprising the steps of:

measuring a vibrational response of the structure;

matching a theoretical response of an idealized system to the measured response; and calculating a modal damping factor of the idealized system having the matched response.

11. The method of claim 10 wherein the step of matching includes the step of fitting a curve to a plurality of measured response data points.

12. The method of claim 11 wherein the step of fitting includes the step of repetitively adjusting the curve to minimize any difference between the curve and the plurality of measured data points.

13. The method of claim 12 wherein the step of fitting includes the step of incrementing any one or more of a modal damping factor, a damped natural frequency, and a maximum amplitude defining the curve between adjustments.

14. The method of claim 13 wherein the step of incrementing includes using a Newton-Raphson computational analysis technique.

15. The method of claim 14 wherein the step of fitting includes the step of determining a difference between the measured data points and the curve using a least squares error evaluation.

16. The method of claim 15 further comprising the step of comparing the calculated modal damping factor with a base modal damping factor.

17. The method of claim 16 wherein the base modal damping factor is a standardized modal damping factor.

18. The method of claim 16 wherein the base modal damping factor is an historical modal damping factor for the structure.

* * * * *